United States Patent
Rose (10) Patent No.: US 7,455,674 B2
(45) Date of Patent: Nov. 25, 2008

(54) HIGH STRENGTH BIORESORBABLES CONTAINING POLY-GLYCOLIC ACID

(75) Inventor: John Rose, Wilberfoss (GB)

(73) Assignee: Smith & Nephew PLC, London (GB)

( * ) Notice: Subject to any disclaimer, the term of this patent is extended or adjusted under 35 U.S.C. 154(b) by 57 days.

(21) Appl. No.: 10/472,908

(22) PCT Filed: Jan. 31, 2003

(86) PCT No.: PCT/GB03/00400

§ 371 (c)(1), (2), (4) Date: Sep. 25, 2003

(87) PCT Pub. No.: WO03/064531

PCT Pub. Date: Aug. 7, 2003

(65) Prior Publication Data

US 2004/0106734 A1    Jun. 3, 2004

(30) Foreign Application Priority Data

Jan. 31, 2002    (GB) .................... 0202233.3

(51) Int. Cl.
- A61F 2/00 (2006.01)
- C08G 63/66 (2006.01)
- C08L 67/04 (2006.01)
- D01D 5/00 (2006.01)

(52) U.S. Cl. ............... 606/76; 264/177.17; 264/177.19; 264/178 F; 264/210.5; 264/210.7; 264/210.8; 264/211.12; 525/450; 528/361; 528/502 B; 528/502 R (58) Field of Classification Search ............ 264/175, 264/176.1, 177.17, 177.19, 177.2, 178 F, 264/210.1, 210.5, 210.7, 210.8, 211.12, 211.21; 525/450; 528/361, 502 B, 502 BR; 606/76
See application file for complete search history.

(56) References Cited

U.S. PATENT DOCUMENTS

| | | | |
|---|---|---|---|
| 3,531,561 A | 9/1970 | Trebu | |
| 3,636,956 A | 1/1972 | Schneider | |
| 3,736,646 A | 6/1973 | Schmitt | |
| 3,797,499 A | 3/1974 | Schnieder | |
| 4,137,921 A | 2/1979 | Okuzumi | |
| 4,181,983 A | 1/1980 | Kulkarni | |
| 4,438,253 A * | 3/1984 | Casey et al. ............. | 528/86 |
| 4,523,591 A | 6/1985 | Kaplan | |
| 4,539,981 A | 9/1985 | Tung | |
| 4,559,945 A | 12/1985 | Koelmel et al. | |
| 4,636,215 A | 1/1987 | Schwartz | |
| 4,700,704 A | 10/1987 | Jamiolkowski et al. | |
| 4,776,329 A | 10/1988 | Treharne | |
| 4,840,632 A | 6/1989 | Kampner | |
| 4,858,603 A | 8/1989 | Clemow et al. | |
| 4,938,763 A | 7/1990 | Dunn et al. | |
| 4,950,258 A | 8/1990 | Kawai et al. | |
| 4,968,317 A * | 11/1990 | Tormala et al. ............. | 606/77 |
| 4,990,161 A | 2/1991 | Kampner | |
| 5,049,591 A | 9/1991 | Hayasai et al. | |
| 5,108,755 A | 4/1992 | Daniels et al. | |
| 5,110,852 A * | 5/1992 | Gogolewski et al. ......... | 524/108 |
| 5,192,301 A | 3/1993 | Kamika | |
| 5,201,738 A | 4/1993 | Scott et al. | |
| 5,201,771 A | 4/1993 | Belykh et al. | |
| 5,266,608 A | 11/1993 | Katz et al. | |
| 5,275,601 A | 1/1994 | Gogolewski et al. | |
| 5,294,395 A | 3/1994 | Broyer | |
| 5,333,624 A | 8/1994 | Tovey | |
| 5,360,448 A | 11/1994 | Thramann | |
| 5,364,400 A | 11/1994 | Rego, Jr. et al. | |
| 5,376,120 A | 12/1994 | Sarver et al. | |
| 5,383,931 A * | 1/1995 | Hehli et al. .............. | 623/17.18 |
| 5,407,445 A | 4/1995 | Tautvydas et al. | |
| 5,417,712 A | 5/1995 | Whittaker | |
| 5,437,918 A | 8/1995 | Taniguchi | |
| 5,441,515 A | 8/1995 | Khosravi | |
| 5,458,653 A | 10/1995 | Davidson | |
| 5,470,334 A | 11/1995 | Ross et al. | |
| 5,522,817 A | 6/1996 | Sander et al. | |
| 5,527,337 A | 6/1996 | Stack et al. | |
| 5,527,341 A * | 6/1996 | Gogolewski et al. ......... | 606/232 |
| 5,562,704 A | 10/1996 | Tamminmaki et al. | |
| 5,571,193 A | 11/1996 | Kampner | |

(Continued)

FOREIGN PATENT DOCUMENTS

| | | |
|---|---|---|
| EP | 0 204 931 B2 | 12/1986 |
| EP | 0 321 389 A1 | 6/1989 |
| EP | 0 401 844 B1 | 12/1990 |
| EP | 0 439 892 A2 | 8/1991 |
| EP | 0 595 956 | 5/1994 |
| EP | 0 531 487 B1 | 1/1996 |
| EP | 0 711 534 A1 | 5/1996 |
| EP | 0 803 521 A1 | 10/1997 |
| EP | 0 805 175 A1 | 11/1997 |

(Continued)

OTHER PUBLICATIONS

Abstract of EP 0751165 A, Bezwada et al. Jan. 2, 1997.*

(Continued)

Primary Examiner—Michael J Feely (57) ABSTRACT

Polymer compositions comprising poly-glycolic acid (PGA) or a functional derivative thereof with a tensile strength of at least 1200 MPa are disclosed. Processes suitable for manufacturing said compositions are also described, comprising rendering PGA into an amorphous state then drawing to form a highly orientated polymer structure. The polymer compositions can be used to make artefacts, for example sutures, or used in combination with other polymers or non-polymeric substances to produce other artefacts, for example medical devices suitable for implantation into the human body. Processes for the production of said artefacts are also described.

32 Claims, 5 Drawing Sheets

U.S. PATENT DOCUMENTS

| | | | |
|---|---|---|---|
| 5,571,204 A | 11/1996 | Nies | |
| 5,633,002 A | 5/1997 | Stricker | |
| 5,634,936 A | 6/1997 | Linden | |
| 5,660,846 A | 8/1997 | Cheikh | |
| 5,670,161 A | 9/1997 | Healy | |
| 5,690,671 A | 11/1997 | McGurk | |
| 5,695,497 A | 12/1997 | Stahelin | |
| 5,716,410 A | 2/1998 | Wang et al. | |
| 5,716,413 A | 2/1998 | Walter et al. | |
| 5,733,330 A | 3/1998 | Cox | |
| 5,760,118 A | 6/1998 | Sinclair | |
| 5,766,239 A | 6/1998 | Cox | |
| 5,766,618 A | 6/1998 | Laurencin et al. | |
| 5,792,400 A | 8/1998 | Talja et al. | |
| 5,834,582 A | 11/1998 | Sinclair | |
| 5,837,276 A | 11/1998 | Carnevale | |
| 5,853,639 A * | 12/1998 | Kawakami et al. | 264/177.19 |
| 5,893,850 A | 4/1999 | Cachia | |
| 5,904,658 A | 5/1999 | Niederauer et al. | |
| 5,908,918 A | 6/1999 | Chen | |
| 5,935,172 A | 8/1999 | Ochoa et al. | |
| 5,968,092 A | 10/1999 | Buscemi | |
| 5,977,204 A * | 11/1999 | Boyan et al. | 523/113 |
| 5,980,564 A | 11/1999 | Stinson | |
| 5,997,580 A | 12/1999 | Mastrorio et al. | |
| 6,001,100 A | 12/1999 | Sherman et al. | |
| 6,001,101 A | 12/1999 | Augagneur et al. | |
| 6,005,161 A | 12/1999 | Brekke et al. | |
| 6,013,080 A | 1/2000 | Khalili | |
| 6,022,352 A | 2/2000 | Vandewalle | |
| 6,071,312 A | 6/2000 | Lampe et al. | |
| 6,077,989 A | 6/2000 | Kandel et al. | |
| 6,113,624 A | 9/2000 | Bezwada et al. | |
| 6,136,369 A * | 10/2000 | Leitao et al. | 427/2.27 |
| 6,150,497 A * | 11/2000 | Sastry et al. | 528/354 |
| 6,160,084 A | 12/2000 | Langer et al. | |
| 6,162,225 A | 12/2000 | Gertzman et al. | |
| 6,187,008 B1 | 2/2001 | Hamman | |
| 6,203,573 B1 | 3/2001 | Walter et al. | |
| 6,248,108 B1 | 6/2001 | Tormala | |
| 6,248,430 B1 | 6/2001 | Toyoda et al. | |
| 6,281,262 B1 | 8/2001 | Shikinami | |
| 6,283,973 B1 | 9/2001 | Hubbard et al. | |
| 6,293,950 B1 | 9/2001 | Lynch et al. | |
| 6,303,697 B1 | 10/2001 | Yuan et al. | |
| 6,315,788 B1 | 11/2001 | Roby | |
| 6,344,496 B1 | 2/2002 | Niederauer et al. | |
| 6,375,465 B1 | 4/2002 | Engman et al. | |
| 6,423,062 B2 | 7/2002 | Enayati | |
| 6,425,923 B1 | 7/2002 | Stalcup et al. | |
| 6,436,136 B1 | 8/2002 | Flodin et al. | |
| 6,468,277 B1 | 10/2002 | Justin et al. | |
| 6,471,707 B1 | 10/2002 | Miller et al. | |
| 6,503,278 B1 | 1/2003 | Pohjonen | |
| 6,511,511 B1 | 1/2003 | Slivka et al. | |
| 6,514,286 B1 | 2/2003 | Leatherbury et al. | |
| 6,565,606 B1 | 5/2003 | Bruce et al. | |
| 6,605,090 B1 | 8/2003 | Trieu et al. | |
| 6,652,582 B1 | 11/2003 | Stinson | |
| 6,719,935 B2 * | 4/2004 | Tunc | 264/40.7 |
| 6,783,712 B2 | 8/2004 | Slivka et al. | |
| 6,827,743 B2 | 12/2004 | Eisermann et al. | |
| 6,841,111 B2 | 1/2005 | Rickner et al. | |
| 6,908,466 B1 | 6/2005 | Bonutti et al. | |
| 6,916,321 B2 | 7/2005 | TenHuisen et al. | |
| 7,033,603 B2 | 4/2006 | Nelson et al. | |
| 7,261,716 B2 | 8/2007 | Strobel et al. | |
| 7,261,734 B2 | 8/2007 | Gellman et al. | |
| 7,268,205 B2 | 9/2007 | Williams et al. | |
| 7,270,813 B2 | 9/2007 | Shimp et al. | |
| 2002/0029043 A1 | 3/2002 | Ahrens et al. | |
| 2002/0123751 A1 | 9/2002 | Fallin | |
| 2002/0150775 A1 | 10/2002 | Ishikawa et al. | |
| 2002/0160032 A1 | 10/2002 | Long et al. | |
| 2003/0045941 A1 | 3/2003 | Lewallen | |
| 2003/0114937 A1 | 6/2003 | Leatherbury et al. | |
| 2003/0125745 A1 | 7/2003 | Tseng et al. | |
| 2003/0236573 A1 | 12/2003 | Evans et al. | |
| 2004/0019386 A1 | 1/2004 | Ferree | |
| 2004/0193154 A1 | 9/2004 | Leatherbury et al. | |
| 2004/0241203 A1 | 12/2004 | Shakesheff et al. | |
| 2004/0242722 A1 | 12/2004 | Rose | |
| 2004/0258732 A1 | 12/2004 | Shikinami | |
| 2004/0260398 A1 | 12/2004 | Kelman | |
| 2004/0265385 A1 | 12/2004 | West | |
| 2004/0267263 A1 | 12/2004 | May | |
| 2005/0008672 A1 | 1/2005 | Winterbottom et al. | |
| 2005/0013793 A1 | 1/2005 | Beckham et al. | |
| 2005/0085313 A1 | 4/2005 | Nishitani | |
| 2005/0107886 A1 | 5/2005 | Crabtree et al. | |
| 2005/0159812 A1 | 7/2005 | Dinger, III, et al. | |
| 2005/0165128 A1 | 7/2005 | Cohn et al. | |
| 2005/0177245 A1 | 8/2005 | Leatherbury et al. | |
| 2005/0209705 A1 | 9/2005 | Niederauer et al. | |
| 2005/0240281 A1* | 10/2005 | Slivka et al. | 623/23.75 |
| 2006/0067973 A1 | 3/2006 | Schachter | |
| 2006/0136071 A1 | 6/2006 | Maspero et al. | |
| 2006/0178748 A1 | 8/2006 | Dinger, III, et al. | |
| 2006/0188547 A1 | 8/2006 | Bezwada | |
| 2006/0200150 A1 | 9/2006 | Homaki et al. | |
| 2006/0247610 A1 | 11/2006 | Lanphere et al. | |
| 2006/0263335 A1 | 11/2006 | France et al. | |
| 2007/0041950 A1 | 2/2007 | Leatherbury et al. | |
| 2007/0043376 A1 | 2/2007 | Leatherbury et al. | |
| 2007/0128154 A1 | 6/2007 | Hadba et al. | |
| 2007/0134305 A1 | 6/2007 | Zilberman | |
| 2007/0191963 A1 | 8/2007 | Winterbottom et al. | |
| 2007/0299156 A1 | 12/2007 | Brown | |
| 2008/0045627 A1 | 2/2008 | Rose | |

FOREIGN PATENT DOCUMENTS

| | | |
|---|---|---|
| EP | 0 806 283 A2 | 11/1997 |
| EP | 1 056 487 B1 | 12/2000 |
| EP | 1 093 774 B1 | 6/2002 |
| EP | 0 815 809 B1 | 3/2004 |
| GB | 807589 | 1/1959 |
| GB | 2319479 | 5/1998 |
| WO | WO 1984/04311 | 11/1984 |
| WO | WO 1990/003768 | 4/1990 |
| WO | WO 1993/01773 | 2/1993 |
| WO | WO 1995/034331 A1 | 12/1995 |
| WO | WO 1997/005193 A1 | 2/1997 |
| WO | WO 1998026814 A1 | 6/1998 |
| WO | WO 1999/011297 A2 | 3/1999 |
| WO | WO 1999/22770 | 5/1999 |
| WO | WO 2001/096105 A2 | 12/2001 |
| WO | WO 2002/076725 | 10/2002 |
| WO | WO 2003/064531 A1 | 8/2003 |
| WO | WO 2004071356 A2 | 8/2004 |
| WO | WO 2005/014718 A1 | 2/2005 |
| WO | WO 2005085313 A1 | 9/2005 |
| WO | WO 2006/053936 | 5/2006 |
| WO | WO 2006/064025 | 8/2006 |
| WO | WO 2007/065074 A2 | 6/2007 |
| WO | WO 2007/084609 A2 | 7/2007 |

OTHER PUBLICATIONS

Abstract of JP 02169612, Asahi Chemical Ind. Jun. 29, 1990.*
Abstract of JP 08196617, Takiron Co. Aug. 6, 1996.*
Abstract of JP 09040761, Shimadzu Corp. Feb. 10, 1997.*
Abstract of JP 09095606, Shinetsu Chemical Co. Apr. 8, 1997.*
Abstract of JP 09234241, Shimadzu Corp. Sep. 9, 1997.*
Abstract of JP 09272790, Shimadzu Corp. Oct. 21, 1997.*

Abstract of JP 09221539, Shimadzu Corp. Aug. 26, 1997.*
Abstract of JP 10176039, Kanebo Ltd. Jun. 30, 1998.*
Abstract of DE 3936188 A1, Boehringer Ingelheim, May 3, 1990.*
Abstract of DE 4226465 A1, Gunze et al. Feb. 11, 1993.*
Abstract of KR 141988 B1, Samyang Co. Ltd. Jun. 15, 1998.*
Andriano, et al., 'Processing and characterization of absorbable polylactide polymers for use in surgical implants,' *Journal of Applied Biomaterials*, 5(2):133-140 (1994).
Asano, et al., 'In vivo characteristics of low molecular weight copoly(D,L-lactic acid) formulations with controlled release of LH-RH agonist,'*Biomaterials*, 10(8):569-573 (1989).
Barca, et al., 'Resorbable poly-L-lactic acid mini-staples for the fixation of Akin osteotomies,' *The Journal of Foot and Ankle Surgery*, 36(2):106-111 (1997).
Bertrand, et al., Biocompatbility Aspects of New Stent Technology, *JACC*, 32(3):562-571 (1998).
Celikkaya, et al., 'Poly(DL-lactide)/Poly(ethylene glycol) Copolymer Particles. I. Preparation and Characterization,' *Journal of Applied Polymer Science*, 61:1439-1446 (1996).
Frenger, 'Biomedical Uses of Shape Memory Polymers,' *Biomed. Sci. Instrum.*, 29:47-50 (1993).
Fukuzaki, et al., Synthesis of copoly(D,L-Lactic acid) with relatively low molecular weight and in vitro degradation, Japan Atomic Energy Research Institute, Gunma, Jpn, European Polymer Journal, 25(10):1019-1026 (1989).
Giardino, et al., 'Experimental evaluation of a resorbable intramedullary plug for cemented total hip replacement,' *Biomaterials*18(13):907-913 (1997).
Gautier, et al., 'Poly($\alpha$-hydroxyacids) for applicationin the spinal cord: Resorbability and biocompatibility with adult rate Schwann cells and spinal cord,' *Journal of Biomedical Materials Research*, 42(4):642-654 (1998).
Haers, et al., 'Biodegradable polyactide plates and screws in orthognathic surgery,' *Journal of Cranio-Maxillofacial Surgery*, 26(2):87-91 (1998).
L. L. Hench, et al., 'Bioactive materials: The potential for tissue regeneration,' *J. Biomed. Materials Research*, 41(4):511-518 (1998).
D. Hull and T. W. Clyne, 'An introduction to composite naterials,' Second Edition, Cambridge University Press, Table of Contents, 8 pages (1996).
Hyon, et al., 'Effects of resudual monomer on the degradation of DL-lactide polymer,' Hyon, Jamshidi & Ikada, *Polymer International*, 46:196-202 (1998).
Kaitian, et al., 'Poly(D,L-Lactic Acid) Homopolymers: Synthesis and Characterization,' *Turkish Journal of Chemistry*, 20:43-53 (1996).
Kister, et al., 'Effects of morphology, conformation and configuration on the IR and Raman spectra of various poly(lactic acid)s, ' *Polymer*, 39(2): 267-273 (1998).
Koelling, et al., 'In vitro real-time aging and characterization of poly(L/D-lactic acid),' *Proceedings of the 1997 16th Southern Biomedical Engineering Conference* (Cat. No. 97th8270), pp. 197-201.
Kontio, et al., 'Fibrous wound repair associated with biodegradable poly-L/D-lactide copolymers implants: study of the expression of tenascin and cellular fibronectin,' *Journal of Materials Science-Materials in Medicine*, 9:10:603-609 (1998).
Kricheldorf, et al., 'Polyactones: 32. High-molecular weight polylactides by ringing-opening polymerization with dibutylmagnesium or butylmagnesium chloride,' *Polymer*, 36(15):2995-3003 (1995).
Losken, et al., 'Memory of DL-polylactic acid biodegradable plates,' *Ann. Plast. Surg.*, 32(6):606-611 (1994).
MacDonald, et al., 'Enzymatic degradability of poly(lactide): Effects of chain stereochemistry and material crystallinity,'*Macromolecules*, 29(23):7356-7361 (1996).
Mainil-Varlet, et al., 'Effect of in vivo and in vitro degradation on molecular and mechanical properties of various low-molecular weight polyactides,' *Journal of Biomedical Materials Research*, 36(3):360-380 (1997).
Matsumura, et al., 'Novel ring opening polymerization of lactide by lipase,' *Macromol. Symp.*, 130:285-304 (1998).

Morita, et al., 'Intravitreous delivery of dexamethasone sodium *m*-sulfobenzoate from poly(DL-lactic acid) implants,' *Biological & Pharmaceutical Bulletin*, 21(2):188-190 (1998).
Okihara, et al., Crystal structure of stereocomplex of poly(L-lactide) and poly(D-lactide), *Journal of Macromolecular Science-Physics*, B30(1-2):119-140 (1991).
Okuzaki, et al., Mechanical Properties and Structure of the Zone-Drawn Poly(L-lactic acid) Fibers, *Journal of Polymer Science, Part B, Polymer Physics*, 37:991-996 (1999).
Oriented Polymer Materials, Edited by Stoyko Fakirov, published by Huthig & Wepf Verlag Zug, Heidelberg, Oxford CT/USA, Table of Contents pp. v, viii, ix-xix (1996).
Penning, et al., 'Preparation and properties of absorbable fibres from L-lactide copolymers,'*Polymer*, 34(5):942-951 (1993).
Pitt, et al., 'Modification of the rates of chain cleavage of poly($\epsilon$-caprolactone) and related polyesters in the solid state,' *Journal of Controlled Release*, 4:283-292 (1987).
Pitto, et al., "Comparison of fixation of the femoral component without cement and fixation with use of a bone-vacuum cementing technique for the prevention of fat embolism during total hip arthroplasty," *J. Bone Joint Surg.*, 81-A(6):831-843 (1999).
Rak, et al., 'The preparation and characterization of poly(DL-lactic acid) for use as a biodegradable drug carrier,' Liverpool Polytech., Liverpool, UK, *Pharmaceutica Acta Helvetiae*, 60:(5-6):162-169 (1985).
Ristic, et al., 'An investigation of synthesis and degradation of poly(D,L-lactide) and controlled release of albumin from biodegradable poly(D,L-lactide) cylinders,' ICheaP-2, the second Italian conference on chemical and process engineering, Florence, pp. 559-563 (1995).
Schliephake, et al., 'Reconstruction of the mandible by prefabricated autogenous bone grafts,' *Int. J. Oral Maxillofac. Surg.*, 26:244-252 (1997).
Stahelin, et al., 'Clinical degradation and biocompatibility of different bioabsorbable interference screws: a report of six cases,' *Arthroscopy: The Journal of Arthroscopic & Related Surgery*, 13(2):238-244 (1997).
Steendam, et al., 'The role of elastic relaxation in drug delivery from poly(DL-lactic acid) based tablets. A shape memory phenomenon,' *Proceedings of the International Symposium on Controlled Release of Bioactive Materials*, 25:128-129 (1998).
Stevels, et al., 'Blends van blok copolymeren die een poly(L-lactide) of poly(D-lactide) blok bevatten,' Biomedical Science and Engineering Meeting, pp. 107-110 (1994).
Tagil, "Thesis - The morselized and impacted bone graft animal experiments on proteins, impaction and load," *Acta Orthop. Scand. Suppl.*, 290:1-40 (2000).
Temenoff and Mikos, "Injectable biodegradable materials for orthopedic tissue engineering," *Biomaterials*, 21:2405-2412 (2000).
Tschakaloff, et al., 'Degradation kinetics of biodegradable DL-polyactic acid biodegradable implants depending on the site of implantation,' *International Journal of Oral and Maxillofacial Surgery*, 23(6Pt2):443-445 (1994).
Tsuji, et al., Stereocomplex formation between enantiomeric poly(lactic acid). VIII. Complex fibers spun from mixed solution of poly(D-lactic acid), *Journal of Applied Polymer Science*, 51(2):337-344 (1994).
J. West, J. Hubbell, 'Bioactive Polymers, Synthetic biodegradable polymer scaffolds,' Chapter 5, pp. 83-95, Anthony Atala and David J. Mooney, Editors; Joseph P. Vacanti and Robert Langer, Associate Editors, Birkhauser (1997).
D. Wheeler, et al., 'Effect of bioactive glass particle size on osseous regeneration of cancellous defects,' *J. Biomed. Materials Research*, 41(4):527-533 (1998).
Zegzula, et al., 'Bone Formationwith Use of rhBMP-2 (Recombinant Human Bone Morphogenetic Protein-2,' *The Journal of Bone and Joint Surgery*, 79:1778-1790 (1997).
Zhang, Biodegradable lactide polymers: synthesis, degradation, and controlled drug release properties (drug release), Queen's University at Kingston, Canada, Volume 55/01-B of Dissertation Abstracts International, p. i-xv, 1-179 (Oct. 1993).

Structure and Properties of Orientated Polymers, Ed. I. M. Ward, Department of Physics, University of Leads, England, a Halsted Press Book, John Wiley & Sons, New York-Toronto (1975) Table of Contents.

Office Action dated Jul. 28, 2008 in related U.S. Appl. No. 10/565,029.

* cited by examiner

HIGH STRENGTH BIORESORBABLES CONTAINING POLY-GLYCOLIC ACID

The present invention relates to polymer compositions and artefacts made therefrom. In particular the present invention relates to polymers having high mechanical strength and their use for the manufacture of load bearing medical devices suitable for implantation within the body. More particularly the invention relates to bioresorbable poly-glycolic acid-containing polymers and to implantable medical devices made therefrom.

Polymer compositions comprising poly-glycolic acid (PGA) have an established use for medical implants. It has also been proposed that certain mechanical properties may be improved by extruding PGA melts or by drawing PGA in a plastic state. Isotropic PGA has a tensile strength of between 50 to 100 MPa and a tensile modulus of between 2 and 4 GPa. A commercial product (SR-PGA) comprising PGA fibres in a PGA matrix has a flex strength and modulus of 200-250 MPa and 12-15 GPa, respectively. It is also reported in the literature that melt spun PGAs have tensile strength of about 750 MPa and a modulus of from 15 to 20 GPa. In U.S. Pat. No. 4,968,317 an example of a drawn PGA is stated to have a tensile strength of about 600 MPa.

Although PGAs having improved strength characteristics are known,. none of the known materials have the mechanical properties approaching those of the metals conventionally used for load bearing implantable medical devices. A commercial alloy used for orthopaedic implant devices, known as Ti-6-4, comprises titanium with 6% aluminium and 4% vanadium and has a tensile strength in the range of 800 to 1000 MPa and a modulus in the order of 1000 Pa.

One possible reason that PGA cannot currently be processed to achieve the desired strength of metals is that when PGA is processed by common methods to produce orientated fibres (e.g. stretching the material at a constant rate in a heated chamber or tank) additional crystallisation of the polymer occurs during the process. The crystals in the polymer act such that they prevent further orientation of the polymer. This crystallisation of the polymer limits the mechanical properties that can be achieved by drawing PGA to around 800 MPa, as described in the prior art.

We have found that polymer compositions comprising PGA may be processed such that the resultant composition has significantly greater strength, typically of the order of greater than 1200 MPa with a commensurate increase in modulus, typically in excess of 22 GPa.

In accordance with the present invention there is provided a polymer composition comprising poly-glycolic acid or a functional derivative thereof having a tensile strength of at least 1200 MPa.

The polymer composition gains this level of tensile strength by means of a novel processing method that results in an orientated structure, for example an orientated fibre.

The present invention further provides an artefact comprising a polymer composition including poly-glycolic acid or a functional derivative thereof having a tensile strength of at least 1200 MPa.

The polymer composition may be comprised entirely of PGA or a derivative thereof, or may comprise a PGA-containing blend with other polymers. Preferably the polymer composition is entirely PGA.

Similarly, artefacts formed from the polymer compositions of the invention may consist wholly of the polymer compositions of the invention or may be composites consisting only partially of the polymer compositions of the invention.

Aptly the artefact contains 10 to 80% by volume of the polymer compositions of the invention, suitably the artefact contains up to 60% by volume of the polymer compositions of the invention, preferably the artefact contains at least 40% by volume of the polymer compositions of the invention and typically the artefact contains approximately 50% by volume of the polymer compositions of the invention.

DETAILED DESCRIPTION OF THE INVENTION

We have found that in order to achieve the high strength exhibited by the compositions of the invention it is necessary that the PGA be rendered into an amorphous state and then immediately drawing to form a highly orientated structure.

This can be achieved by first processing isotropic PGA granules, which are commercially available, to form fibres or filaments, thereafter passing the fibres into a quenching bath to form an amorphous structure. Polymer compositions of the present invention may then be produced by drawing the quenched, amorphous PGA. Preferably this is a drawing process which minimises the time polymer is exposed to elevated temperatures, thus minimising the time for the polymer to crystallise.

In accordance with another aspect of the invention there is provided a process for the manufacture of poly-glycolic acid-based polymer compositions comprising increasing polymer chain orientation of a substantially amorphous polymer by drawing at localized points within the mass.

Suitably this comprises the steps of forming poly-glycolic acid or a functional derivative thereof into fibres, for example by melt extrusion or solution spinning; quenching the fibres then subjecting the quenched fibres to a tension under conditions whereby a defined region of the tensioned fibres is drawn.

Aptly fibres of amorphous PGA-containing polymers may be prepared by solution spinning or melt extruding the polymer through a die; the filament is then rapidly chilled to produce a substantially amorphous material. Typical chilling methods include blowing a cold gas onto the filament as it is produced or by passing the filament through a bath of a suitable cold liquid, e.g. water, silicone oil.

Figure 1:
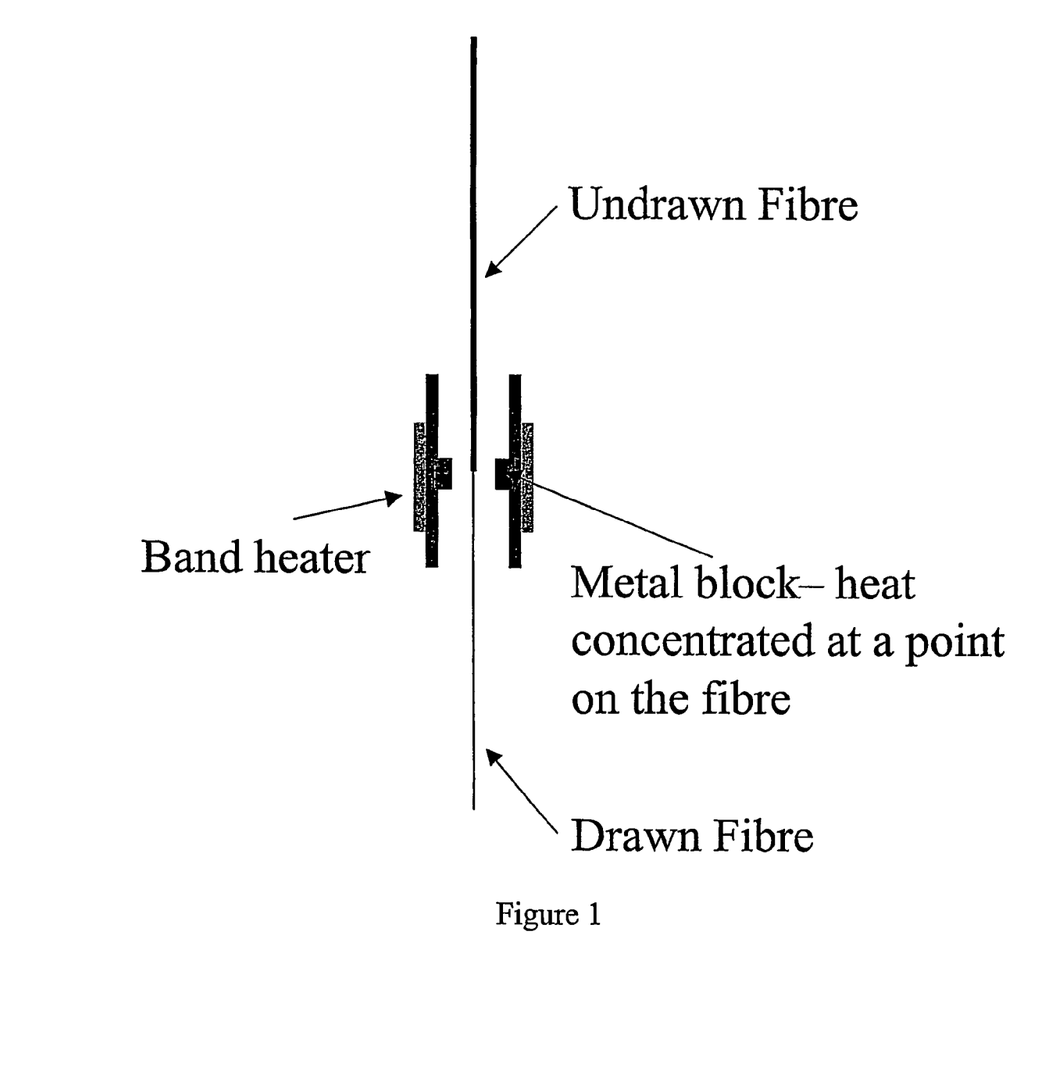
FIG. 1 depicts an embodiment wherein the fibre is locally heated.
Figure 2:
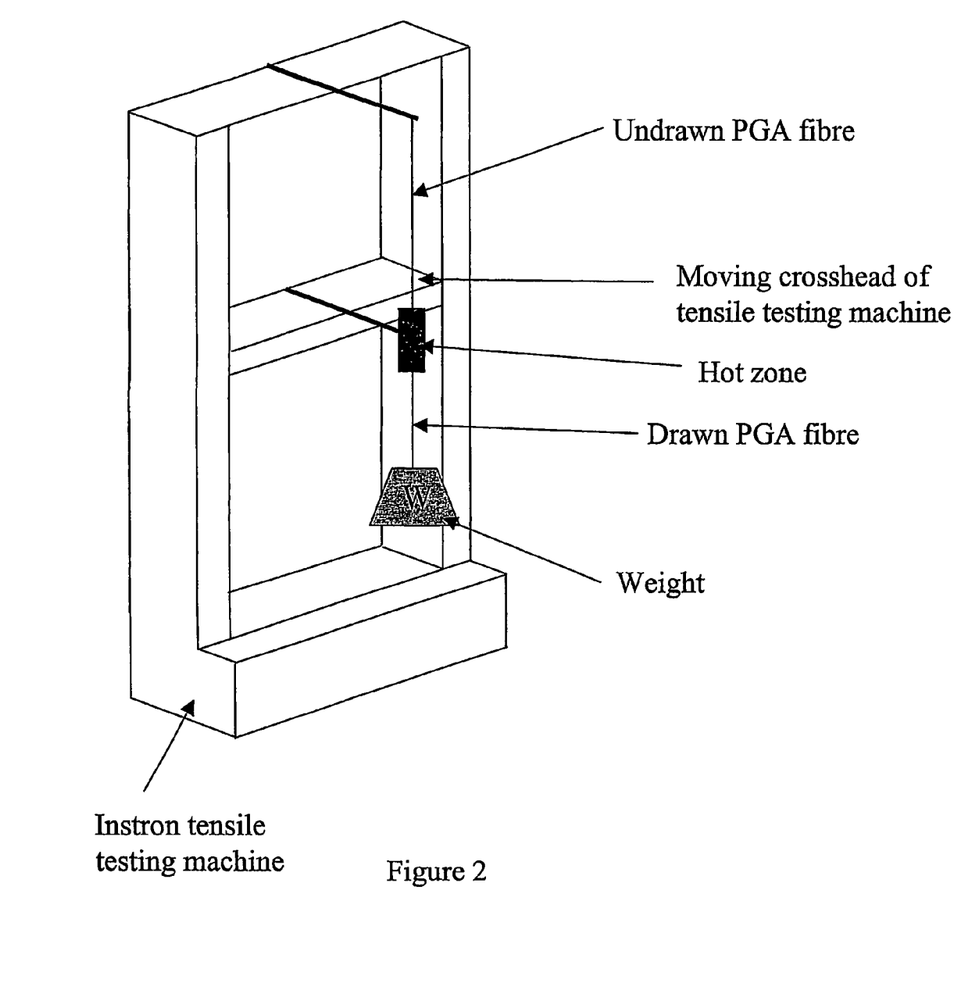
FIG. 2 depicts an embodiment wherein the fibre is drawn by a weight.

A suitable drawing method is zone heating. In this process a localised heater is moved along a length of fibre which is held under constant tension. This process is used in the zone-drawing process as described by Fakirov in Oriented Polymer Materials, S Fakirov, published by Hüthig & Wepf Verlag, Hüthig GmbH. In order to carry out this zone heating fibre can be passed through a brass cylinder. A small part of the cylinder inner wall is closer to the fibre, this small region locally heats the fibre, compared to the rest of the brass cylinder, localising the drawing of the fibre to this location, see FIG. 1. A band heater can be placed around the brass cylinder to allow it to be heated above room temperature. This heated brass cylinder can then be attached to the moving cross-head of a tensile testing machine and the fibre to be drawn suspended from a beam attached to the top of the testing machine. To draw the fibre a weight can be attached to the lower end of the fibre, the brass cylinder heated to the desired temperature and the cross-head moved to the lower end of the fibre, see FIG. 2. The polymer draws where the fibre is closest to the brass cylinder, as the cross-head is moved up the length of the fibre, then a length of the fibre can be drawn.

Suitably the fibre can be held taut using a small stress, which is typically below the yield point of the material at ambient temperatures. The fibre can then be heated locally to a temperature which is above the softening point ($T_g$) but below the melting point such that localised drawing of the polymer occurs, the whole fibre can be treated by movement of either or both the fibre and heated zone such that the full length of the fibre is drawn. This first drawing of the polymer may produce a polymer with improved molecular alignment and therefore strength and modulus. In this first step the conditions are selected such that the material does not substantially crystallise during the process, this requires that either the temperature of the polymer is below the temperature at which crystallisation occurs, $T_c$, or if the polymer is above $T_c$ the speed at which the heated zone moves along the fibres is fast enough such that the polymer cools below $T_c$ before it has time to crystallise. Further improvements can be made by subsequent treatments, where the stress applied to the fibre or the zone temperature is increased or both. Both the strength of the fibre and the softening point increase as the degree of molecular alignment improves. The process can be repeated many times, until the desired properties are reached. A final annealing step can be carried out in which the material crystallises under tension in the process; this can further improve the mechanical properties and improve the thermal stability of the final fibre.

In an embodiment of this aspect of the invention there is provided an artefact comprising a poly-glycolic acid in accordance with the invention. For example, the poly-glycolic acid fibres can be mixed with other components to form the artefacts. These other components may be polymers, co-polymers, bioresorbable polymers, non-polymeric materials or combinations thereof.

Aptly the bioresorbable polymer comprises a poly-hydroxy acid, a poly-lactic acid, a poly-caprolactone, a polyacetal, a poly-anhydride or mixture thereof; the polymer comprises poly-propylene, poly-ethylene, poly-methyl methacrylate, epoxy resin or mixtures thereof whilst the non-polymeric component comprises a ceramic, hydroxyapatite, tricalcium phosphate, a bioactive factor or combinations thereof.

Suitably the bioactive factor comprises a natural or engineered protein, a ribonucleic acid, a deoxyribonucleic acid, a growth factor, a cytokine, an angiogenic factor or an antibody.

Artefacts according to the present invention can aptly be manufactured by placing appropriate lengths of strengthened PGA fibre into moulds, adding the other components then compression moulding. Alternatively, the strengthened fibres can be pre-mixed with the other components then compression moulded.

In an alternative processing method, artefacts according to the present invention can be manufactured by forming a polymeric component in the presence of the strengthened fibres by in situ curing of monomers or other precursors for said polymeric component.

Preferably the monomers used in this process do not liberate any by-products on polymerisation as these can compromise the properties of the artefact.

Aptly at least one of the monomers used in said in situ curing process is a ring-opening monomer that opens to form a poly-hydroxy acid. Typically at least one monomer is a lactide, a glycolide, a caprolactone, a carbonate or a mixture thereof.

The polymer compositions of the invention are useful for the production of medical devices, particularly implantable devices where it is desirable or necessary that the implant is resorbed by the body. Thus, artefacts in accordance with the present invention include sutures; tissue-engineering scaffolds or scaffolds for implantation; orthopaedic implants; reinforcing agents for long fibre composites used in resorbable load bearing orthopaedic implants; complex shaped devices, for example formed by injection moulding or extruding composites formed by mixing short lengths of chopped fibres with poly-lactic acid; or bone fixation devices, for example formed from relatively large diameter rods (e.g., greater than 1 mm) of the compositions of the invention.

The invention will now be illustrated by the following examples.

EXAMPLE 1

Figure 3:
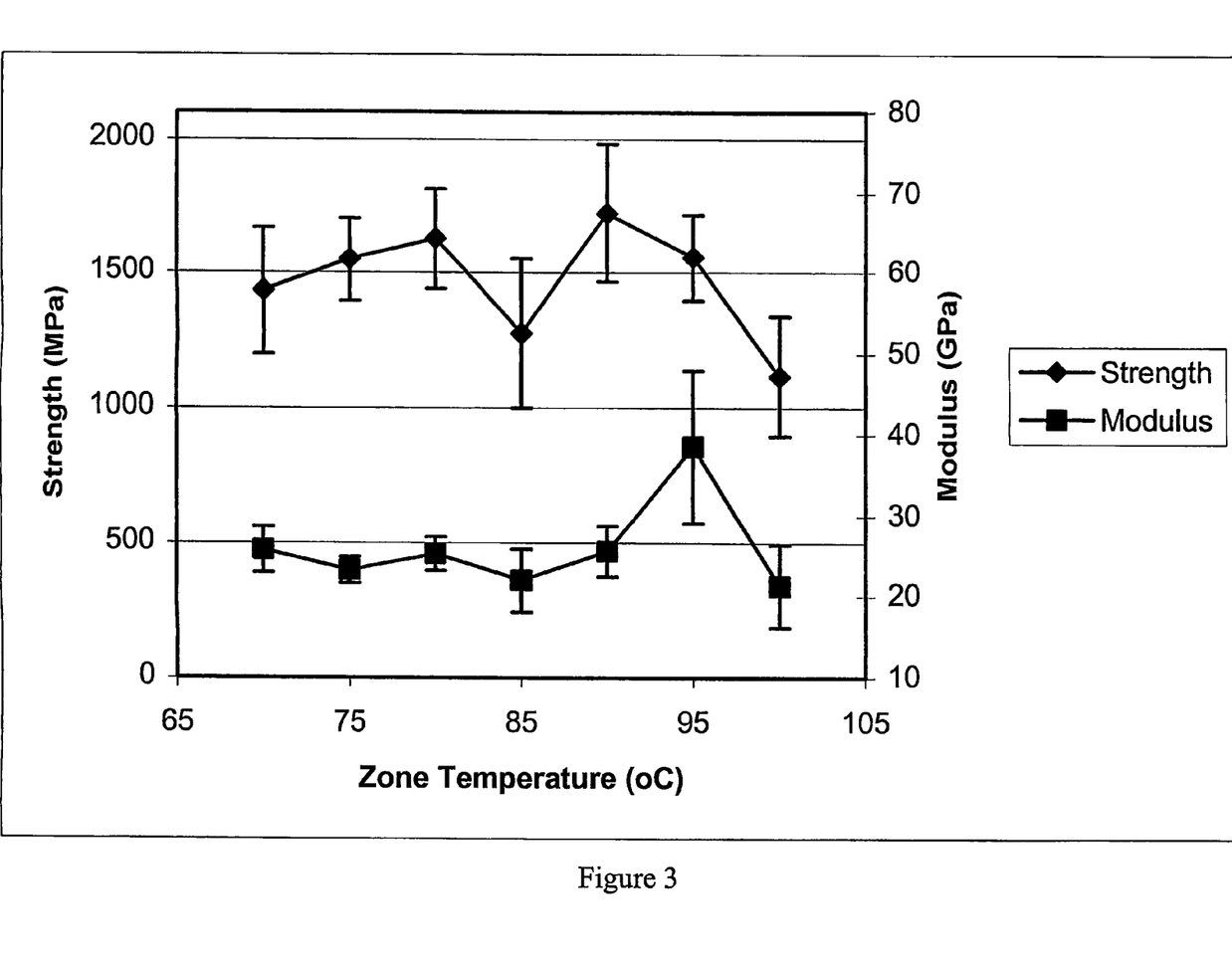
FIG. 3 shows strength and modulus values in relation to zone temperature.

Isotropic PGA was extruded into a water bath to produce a translucent fibre of approx 0.5 mm diameter. This fibre was then suspended vertically and a weight of 200 g was applied. A heated cylinder of brass with a hole of approx 15 mm apart from a small section with a 2 mm diameter hole, through which the PGA fibre passes, was heated to a temperatures between 70° C. and 100° C. and moved along the fibre at a speed of 300 mm/min. The fibres were still translucent after this process, with the exception of the fibre processed with the bass cylinder set to a temperature of 100° C. which was opaque. The resultant fibres were tested by mounting them at 22° C. in a Zwick tensile testing machine, such that the length of fibre between the grips was 40 mm. The sample was then pulled at a rate of 10 mm/min. The resultant load extension curve was recorded and the maximum load recorded was used to calculate the maximum strength of the fibre and the initial slope was used to calculate the modulus of the sample. The results are shown in FIG. 3.

EXAMPLE 2

Isotropic PGA was extruded into a water bath to produce a translucent fibre of approx 0.5 mm diameter. This fibre was then suspended vertically and a weight of 200 g was applied. A heated cylinder of brass with a hole of approx 15 mm apart from a small section with a 2 mm diameter hole, through which the PGA fibre passes, was heated to a temperature of 90° C. and moved along the fibre at a speed of 500 mm/min. The resultant fibre was still translucent after this process. The fibre produced was tested, as described below, and found to have a strength of 1780 MPa and a modulus of 26.7 GPa.

EXAMPLE 3

PGA fibre was produced as in example 2, and then the drawn PGA fibre was re-drawn using a temperature of 90° C. and a speed of 500 mm/min for the zone, with a weight of 500 g applied to the fibre. The fibre produced was opaque indicating that crystallization of the polymer had occurred in this process step. When tested the fibres were found to have a strength of 2400 MPa and a modulus of 40.8 GPa.

EXAMPLE 4

Figure 4:
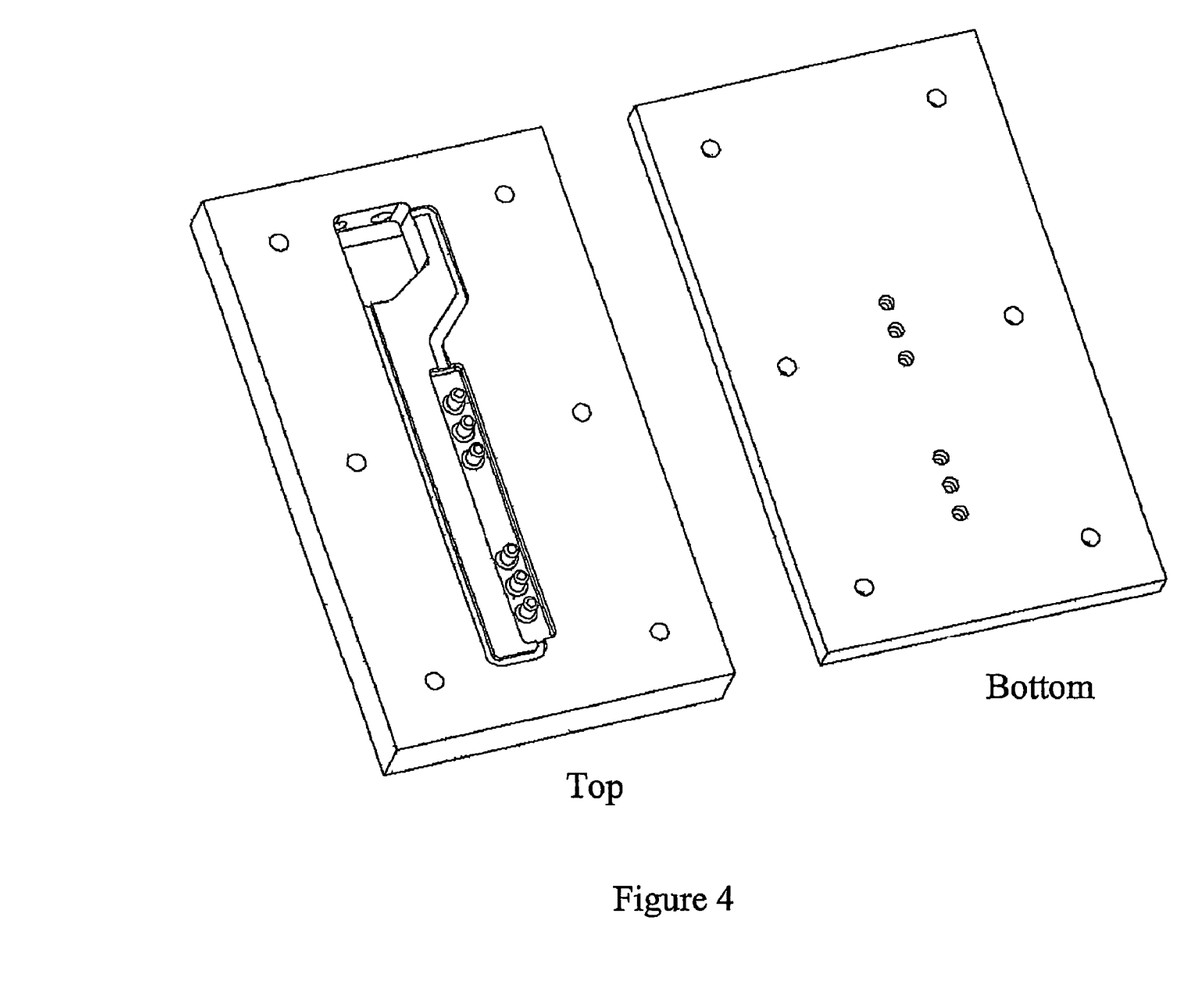
FIG. 4 shows a two-part mould for a fixation plate.

A block of PTFE was machined to form a two-part mould for a fixation plate, see FIG. 4. A reaction mixture was prepared by weighing 100 g of DL-Lactide into a glass vial in a dry nitrogen atmosphere and sealed with a septum. 10 µl of a solution of SnCl2.2H2O (1.00 g) in Di(ethylene glycol) (2.91 g) were then injected into the monomer vial using a 25 µl syringe. The vial was then heated in an oven at 150° C., once the monomer had completely melted; the vial was shaken to mix the contents. Braided fibres of drawn PGA, as made in Example 2, were first packed into the mould cavity (corresponding to 45% of the mould volume) and then the mould was placed in an oven at 150° C. Once the mould at reached temperature, the molten reaction mixture and mould were placed in a dry nitrogen atmosphere and the reaction mixture poured into the mould before either had cooled sufficiently for the monomer to crystallise. The filled mould was sealed then returned to the 150° C. oven, vented by piercing the cap with a syringe needle. To remove air bubbles from the fibre in the mould, the hot mould was transferred to a vacuum oven at 150° C. A vacuum of 1 mbar was applied, the oven was then re-pressurised with dry nitrogen; this was repeated once. The mould was then removed from the oven and the syringe needle vent removed. The mould was then placed in a conventional oven at 150° C. for 6 days to cure the polymer.

After curing the mould was removed from the oven and allowed to cool to room temperature. The mould was then separated and the device removed from the mould. The DL-lactide had polymerized to form a translucent solid phase around the fibres.

EXAMPLE 5

Using the same mould as for example 4 a fixation plate was made using L-lactide as the monomer precursor for the matrix. The catalyst, initiator and curing conditions were identical to those used in example 4. When the plate was removed from the mould it could be seen that the L-lactide had polymerized to form an opaque solid around the fibres.

EXAMPLE 6

Figure 5:
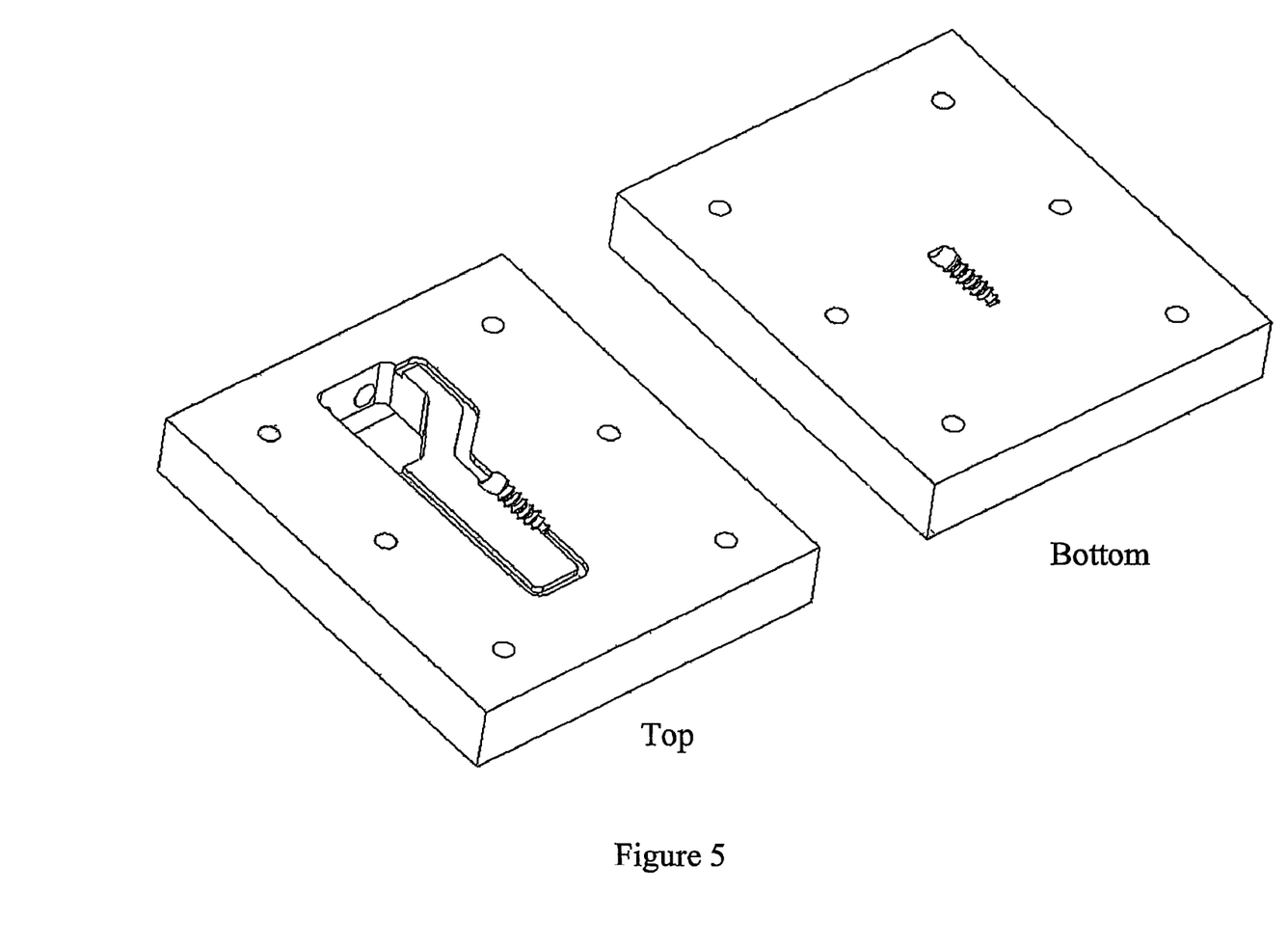
FIG. 5 shows a two-part mould for a RCI screw.

A block of PTFE was machined to form a two-part mould for a RCI screw, see FIG. 5. The catalyst, initiator and curing conditions used were identical to example 4 but the material used to form the matrix was a mixture of DL-lactide and glycolide in the ratio 85:15. Short fibres of drawn PGA (approx 2 mm long), as made in example 2, were packed into the mould (corresponding to 30% of the mould volume). Once curing was complete the mould was left to cool and the device removed. The monomers had cured to form a solid translucent phase around the fibres.

The invention claimed is:

1. A polymer composition comprising poly-glycolic acid or a functional derivative thereof, both (1) in an oriented fibre form or an oriented filament form and (2) having a tensile strength of at least 1200 MPa.

2. A polymer composition of claim 1 wherein the poly-glycolic acid or functional derivative thereof is in an oriented fibre form and further featuring a tensile modulus of at least 22 GPa.

3. An artifact comprising poly-glycolic acid or a functional derivative thereof, both (1) in an orientated fibre form or an oriented filament form and (2) having a tensile strength of at least 1200 MPa.

4. An artifact of claim 3 further comprising at least one additional polymer component.

5. An artifact of claim 3, wherein the artifact is in the form of a medical device.

6. An artifact of claim 5, wherein the device is a suture, a scaffold for tissue engineering or implantation, an orthopedic implant, a complex shaped device or a bone fixation device.

7. A process for the manufacture of a polymer composition comprising the steps of: forming poly-glycolic acid or a functional derivative thereof into fibres; quenching the fibres; and subjecting the quenched fibres to a tension under conditions whereby a defined region of the tensioned fibres is drawn; wherein the resulting polymer composition is the from of an oriented fibre having a tensile strength of at least 1200 MPa.

8. A process according to claim 7 wherein the fibre-forming method is melt extrusion or solution spinning.

9. A process according to claim 7 wherein the quenched, tensioned fibres are subjected to zone-heating.

10. A process according to claim 7 wherein the quenched, tensioned fibres are subjected to at least two separate drawing steps, each drawing step performed under identical or different conditions.

11. A process for the manufacture of a polymer composition comprising the steps of: forming poly-glycolic acid or a functional derivative thereof into fibres; quenching the fibres to form an amorphous structure; and subjecting the quenched fibres to a tension under conditions whereby a defined region of the tensioned fibres is drawn; wherein the fibres are drawn in a manner to minimize the time the polymer is exposed to elevated temperature; and wherein the resulting polymer composition is the from of an oriented fibre having a tensile strength of at least 1200 MPa.

12. An artifact comprising the polymer composition produced by the process of claim 11.

13. A process for the manufacture of a polymer composition comprising the steps of: forming poly-glycolic acid or a functional derivative thereof into fibres; quenching the fibres to form an amorphous structure; and subjecting the quenched fibres to a tension under conditions whereby a defined region of the tensioned fibres is drawn; wherein drawing at localized points within the amorphous structure results in increased polymer orientation; and wherein the resulting polymer composition is the from of an oriented fibre having a tensile strength of at least 1200 MPa.

14. An artifact comprising the polymer composition produced by the process of claim 13.

15. An artifact of claim 14 further comprising at least one additional polymer component.

16. An artifact of claim 15, wherein the polymer composition produced by the process of claim 4 accounts for 10-80% by volume of the artifact.

17. An artifact of claim 15 wherein at least one of the polymer components is a co-polymer, or polymer blend.

18. An artifact of claim 15, wherein at least one of the polymer components is bioresorbable.

19. An artifact of claim 18, wherein the bioresorbable polymer comprises a poly-hydroxy acid, a poly-lactic acid, a poly-caprolactone, a poly-acetal or a poly-anhydride.

20. An artifact of claim 14 further comprising at least one non-bioresorbable polymer component.

21. An artifact of claim 20, wherein the non-bioresorbable polymer comprises poly-propylene, poly-ethylene, poly-methyl methacrylate or epoxy resin.

22. An artifact of claim 14 further containing at least one non-polymeric component.

23. An artifact of claim 22, wherein the non-polymeric component comprises a ceramic, hydroxyapatite or tricalcium phosphate.

24. An artifact of claim 22, wherein the non-polymeric component comprises a bioactive component.

25. An artifact of claim 24, wherein the bioactive component comprises a natural or engineered protein, a ribonucleic acid, a deoxyribonucleic acid, a growth factor, a cytokine, angiogenic factor or an antibody.

26. An artifact of claim 14, wherein the artifact is in the form of a medical device.

27. An artifact of claim 26, wherein the device is a suture, a scaffold for tissue engineering or implantation, an orthopedic implant, a complex shaped device or a bone fixation device.

28. A process for the manufacture of artifacts comprising the steps of: (1) adding the following materials to a mold: the polymer composition produced by the process of claim 4; and at least one additional component selected from the group consisting of polymers and non-polymeric materials; and (2) performing compression molding.

29. A process for the manufacture of artifacts comprising the steps of: (1) adding the following materials to a mold: the polymer composition produced by the process of claim 4; and at least one additional component selected from the group consisting of monomers and other polymer precursors; (2) performing in situ curing of the monomers or other polymer precursors in the mold to produce a polymer component; and (3) performing compression molding.

30. A process according to claim 29, wherein the monomers do not liberate a by-product during polymerization.

31. A process according to claim 29, wherein at least one of the monomers is a ring-opening monomer that opens to form a poly-hydroxy acid.

32. A process according to claim 29, wherein at least one monomer is a lactide, a glycolide, a carbonate or mixtures thereof.

* * * * *

UNITED STATES PATENT AND TRADEMARK OFFICE
CERTIFICATE OF CORRECTION

PATENT NO. : 7,455,674 B2
APPLICATION NO. : 10/472908
DATED : November 25, 2008
INVENTOR(S) : John Rose Page 1 of 1

It is certified that error appears in the above-identified patent and that said Letters Patent is hereby corrected as shown below:

Claim 16, column 6, line 46:
    Delete "4" and insert -- 13 -- in place thereof.

Claim 28, column 7, line 14:
    Delete "4" and insert -- 13 -- in place thereof.

Claim 29, column 8, line 3:
    Delete "4" and insert -- 13 -- in place thereof.

Signed and Sealed this

Twenty-eighth Day of April, 2009

JOHN DOLL
*Acting Director of the United States Patent and Trademark Office*